United States Patent [19]

Sagawa et al.

[11] Patent Number: 5,556,980
[45] Date of Patent: Sep. 17, 1996

[54] PIPERIDINE COMPOUND, A PROCESS FOR PRODUCING THE SAME AND A STABILIZER USING THE SAME

[75] Inventors: Seiji Sagawa, Chiba; Toshio Kano, Kanagawa; Motohiko Samizo, Osaka; Fumitoshi Kojima, Osaka; Tetsuo Yamaguchi, Osaka, all of Japan

[73] Assignees: Sumitomo Chemical Co., Ltd., Osaka; Kyodo Chemical Co., Ltd., Tokyo, both of Japan

[21] Appl. No.: 294,829

[22] Filed: Aug. 29, 1994

[30] Foreign Application Priority Data

Sep. 3, 1993 [JP] Japan .................................. 5-219796
Dec. 24, 1993 [JP] Japan .................................. 5-329083

[51] Int. Cl.⁶ .............................................. C07D 211/30
[52] U.S. Cl. ........................................................ 546/190
[58] Field of Search .............................................. 546/190

[56] References Cited

U.S. PATENT DOCUMENTS 4,500,662  2/1985  Lai .
4,601,839  7/1986  Lai .
5,049,604  9/1991  Fujii et al. .

FOREIGN PATENT DOCUMENTS 2136805  9/1984  United Kingdom .

*Primary Examiner*—Philip Tucker
*Assistant Examiner*—Catherine Kilby Scalzo
*Attorney, Agent, or Firm*—Watson Cole Stevens Davis, P.L.L.C.

[57] ABSTRACT

2-Methyl-3-(2,2,6,6-tetramethyl-4-piperidylamino)-N-(2,2,6,6-tetramethyl-4-piperidyl)-propionamide represented by the following formula, a process for producing the same and a stabilized organic material composition containing the same wherein the piperidine compound imparts excellent properties, such as light stability or thermal stability to the organic materials.

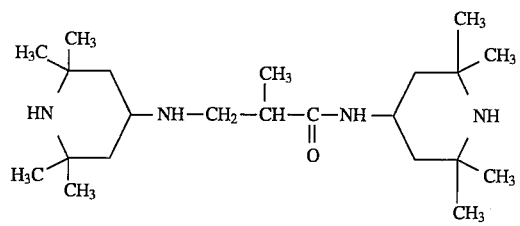

1 Claim, No Drawings

PIPERIDINE COMPOUND, A PROCESS FOR PRODUCING THE SAME AND A STABILIZER USING THE SAME

The present invention relate to a novel piperidine compound, a process for producing the same and its use as a stabilizer for organic materials.

Many organic materials, such as synthetic resins, synthetic rubbers, paints, waxes and the like, are easily deteriorated by light. In order to prevent such deterioration, various types of stabilizer have been used. As the typical examples of the stabilizer, hindered amine light stabilizer, benzotriazole ultraviolet absorber, benzophenone ultraviolet absorber and the like have been known.

An object of the present invention is to provide a novel compound which imparts excellent light resistance as well as excellent heat resistance to the organic materials by blending the compound to the materials.

Another object of the present invention is to provide a process for producing the compound which exhibits above-mentioned excellent properties from commonly-used starting materials through a common reaction which can be easily carried out.

A further object of the present invention is to provide a method for stabilizing organic materials, particularly those which are easily deteriorated by light, by using the compound.

The present inventors have made extensive studies to attain the above-mentioned objects and, as the result, found a novel compound having a hindered piperidine skeleton and attained the present invention.

The present invention provides 2-methyl-3 -(2,2,6,6-tetramethyl-4-piperidylamino)-N-(2,2,6,6 -tetramethyl-4-piperidyl)-propionamide represented by the following formula.

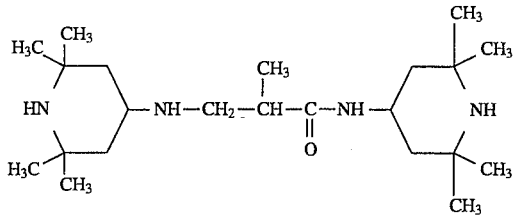

The piperidine compound above-mentioned can be effectively used for stabilizing organic materials, particularly for those which tend to be deteriorated by light. Accordingly the present invention also provides a stabilizer containing the piperidine compound as an active ingredient, and the present invention further provides an organic material composition comprising an organic material to be stabilized and effective amount of above-mentioned piperidine compound as a stabilizer.

The piperidine compound of the present invention can be produced according to a process similar to known methods. It can also be produced by allowing 4-amino-2,2,6,6-tetramethylpiperidlne to react with methacrylic acid. In this reaction, not only an addition reaction is allowed between the double bond of the methacrylic acid and the primary amino group of the 4-amino-2,2,6,6 -tetramethylpiperidine but also dehydrate-amidation is allowed between the carboxyl group of the methacrylic acid and the primary amino group of the 4-amino-2,2,6,6 -tetramethylpiperidine. Accordingly, in this reaction, 4-amino-2,2,6,6-tetramethylpiperidine should preferably be used in an amount of from about 2 to 2.2 moles per 1 mole of methacrylic acid. The reaction is exothermic reaction and is usually carried out at a temperature of from about 120° to 80° C. under atmospheric pressure while distilling off the water generated from the dehydrate-amidation. The reaction is terminated when theoretical amount of water has been distilled off. The reaction can be carried out under atmospheric condition or in an inert gas, such as nitrogen.

As mentioned above, the piperidine compound of the present invention can be effectively used for stabilizing organic materials, particularly those which are easily deteriorated by light, such as synthetic resins, natural or synthetic rubbers, paints, waxes, oils or the like. As the examples of the organic materials to be stabilized according to the present invention, the following can be mentioned, but it is to be understood that the organic materials are not limited to the following:

(1) polyethylene, such as high-density polyethylene (HD-PE), low-density polyethylene (LD-PE), linear low-density polyethylene,
(2) polypropylene,
(3) methylpentenepolymer,
(4) EEA resin (ethylene-ethylacrylate copolymer),
(5) ethylene-vinylacetate copolymer,
(6) polystyrenes such as polystyrene, poly(p-methylstyrene), poly($\alpha$-methylstyrene),
(7) AS resin (acrylonitrile-styrene copolymer),
(8) ABS resin (acrylonitrile-butadiene-styrene copolymer),
(9) AAS resin (blend of acryl rubber and acrylonitrile-styrene copolymer),
(10) ACS resin (acrylonitrile-chlorinated polyethylene-styrene copolymer),
(11) chlorinated polyethylene, polychloroprene, chlorinated rubber,
(12) polyvinylchloride, polyvinylidene chloride,
(13) methacryl resin,
(14) ethylene-vinylalcohol copolymer,
(15) fluoride resin,
(16) polyacetal,
(17) polyphenylene ether resin, polyphenylene sulfide resin,
(18) polyurethane,
(19) polyamide,
(20) poethyleneterephthalate, pobutyleneterephthalate,
(21) polycarbonate,
(22) polyacrylate,
(23) polysulfone, polyetheretherketone, polyethersulfone,
(24) aromatic polyester resin,
(25) epoxy resin,
(26) diallylphthalate prepolymer,
(27) silicone resin,
(28) unsaturated polyester resin,
(29) acrylic benzoguanamine resin,
(30) benzoguanamine-melamine resin,
(31) urea resin,
(32) polybutadiene,
(33) 1,2-polybutadiene,
(34) polyisoprene,
(35) styrene-butadiene copolymer,
(36) butadiene-acrylonitrlle copolymer,
(37) ethylene-propylene copolymer,
(38) silicone rubber,
(39) epichlorohydrin rubber,
(40) acryl rubber,
(41) chlorine rubber coating,
(42) polyester resin coating,
(43) urethane resin coating,
(44) epoxy resin coating,
(45) acryl resin coating,

(46) vinyl resin coating,
(47) aminoalkyd resin coating,
(48) alkyd resin coating,
(49) nitrocellulose resin coating,
(50) oil alkyd coating,
(51) wax, and
(52) synthetic oil for lubricant Suitable amount of the piperidine compound to be added to the organic materials in order to stabilize them varies depending on the types of the materials. In the usual case, preferable amounts of the piperidine compound to be added are from about 0.01 to 2 weight parts per 100 weight parts of the organic materials, because, usually, when the amount is less than 0.01 weight part, the stabilizing effect is not satisfactory and on the other hand, even when the amount exceeds 2 weight parts, the effect is not greatly improved, so increasing the amount beyond 2 weight parts causes economical disadvantage.

The organic materials containing the piperidine compound according to the present invention may further contain one or more other types of additives, such as an antioxidant, ultraviolet absorber, a hindered amine light stabilizer, a metallic inactivator, a metallic soap, a lubricant, a nucleating agent, an epoxy compound, a plasticizer, a flame retardant, an antistatic agent, a foaming agent, a pigment, a fluorescent brightening agent, an inorganic filler, an organo tin stabilizer, an organo metal stabilizer, auxiliary stabilizer or the like.

Examples of the antioxidant preferably used together with the piperidine compound in the present invention include phenolic-type antioxidants, phosphorous containing antioxidants, and the like. As examples of the phenolic-type antioxidants, the following can be mentioned but should not be considered limiting:

octadecyl 3-(3,5-di-t-butyl-4-hydroxyphenyl)propionate,
3,9-bis[2-{3-(3-t-butyl-4-hydroxy-5-methylphenyl)propionyloxy}-1,1-dimethylethyl]-2,4,8,10 -tetraoxaspiro[5.5] undecane,
pentaerythrityl tetrakis[3-(3,5-di-t-butyl-4-hydroxyphenyl) propionate],
2-(3,5-di-t-butyl-4-hydroxyanilino)-4,6-bis(n-octylthio)-1, 3,5-triazine,
triethyleneglycol bis[3-(3-t-butyl-4-hydroxy-5-methylphenyl)propionate],
hexamethylene bis[3-(3,5-di-t-butyl-4-hydroxyphenyl)propionate],
2,2'-thiodiethylene bis[3-(3,5-di-t-butyl-4-hydroxyphenyl) propionate],
1,3,5-tris(3,5-di-t-butyl-4-hydroxybenzyl)isocyanurate,
1,3,5-tris(4-t-butyl-3-hydroxy-2,6-dimethylbenzyl)isocyanurate,
1,3,5-tris[2-{3-(3,5-di-t-butyl-4-hydroxyphenyl) propionyloxy}ethyl]isocyanurate,
1,3,5-tris(3,5-di-t-butyl-4-hydroxybenzyl) 2,4,6-trimethylbenzene,
2-t-butyl-6-(3-t-butyl-2-hydroxy-5-methylbenzyl)-4-methylphenyl acrylate,
2-[1-(2-hydroxy-3,5-di-t-pentylphenyl)ethyl]-4,6-di-t-pentylphenyl acrylate,
1,1,3-tris(5-t-butyl-4-hydroxy-2-methylphenyl) butane
bis[2-t-butyl-4-methyl-6-(3-t-butyl-2-hydroxy-5-methylbenzyl)phenyl]terephthalate,
2,6-di-t-butyl-4-methylphenol,
2,2'-methylenebis(6-t-butyl-4-methylphenol),
2,2'-methylenebis(6-t-butyl-4-ethylphenol),
2,2'-methylenebis[6-(1-methylcyclohexyl)-4-methylphenol],
4,4'-butylidenebis(2-t-butyl-5-methylphenol),
4,4'-thiobis(2-t-butyl-5-methylphenol),
2,2'-thiobis(6-t-butyl-4-methylphenol),
2,2'-ethylidenebis(4,6-di-t-butylphenol),
2,2'-ethylidenebis(4-sec-butyl-6-t-butylphenol),
and the like.

As examples of the phosphorous containing antioxidants, the following can be mentioned but should not be considered limiting:
tris(nonylphenyl)phosphite,
tris(2,4-di-t-butylphenyl)phosphite,
tetrakis(2,4-di-t-butylphenyl) 4,4'-biphenylene diphosphonite,
bis(2,4-di-t-butylphenyl)pentaerythritol diphosphite,
bis(2,6-di-t-butylphenyl)pentaerythritol diphosphite,
distearyl pentaerythritol diphosphite,
phenyl diisooctyl phosphite,
phenyl diisodecyl phosphite,
phenyl di(tridecyl)phosphite,
diphenyl isooctyl phosphite,
diphenyl isodeoyl phosphite,
diphenyl tridecyl phosphite,
4,4'-isopropylidenediphenyl tetraalkyl diphosphite,
2,2'-methylenebis(4,6-di-t-butylphenyl)octyl phosphite,
2,2'-ethylidenebis(4,6-dt-t-butylphenyl)fluoro phosphonite,
and the like.

A sulfur-containing antioxidants may be used together with the piperidine compound if its amount is so small that it and the piperidine compound do not cause antagonism. It can be usually used if the amount is about 0.1 weight part or less per 1 weight part of the piperidine compound.

As examples of the sulfur-containing antioxidants usable in the present invention, the following can be mentioned but should not be considered limiting:
dilauryl 3,3'-thiodipropionate,
dimyristyl 3,3'-thiodipropionate,
distearyl 3,3'-thiodipropionate,
tetrakis(3-laurylthiopropionyloxymethyl)methane,
and the like.

Examples of the ultraviolet absorber usable together with the piperidine compound in the present invention include a benzophenone-type ultraviolet absorber, a benzotriazole-type ultraviolet absorber and the like. As examples of the benzophenone-type ultraviolet absorber, the following can be mentioned but should not be considered limiting:
2-hydroxy-4-methoxybenzophenone,
2-hydroxy-4-octyloxybenzophenone,
2,2'-dihydroxy-4-methoxybenzophenone,
bis(5-benzoyl-4-hydroxy-2-methoxyphenyl)methane,
2,2',4,4'-tetrahydroxybenzophenone,
and the like.

As examples of the benzotriazole-type ultraviolet absorber, the following can be mentioned but should not be considered limiting:
2-(2-hydroxy-5-methylphenyl)benzotriazol,
2-[2-hydroxy-3-(3,4,5,6-tetrahydrophthalimidomethyl)-5-methylphenyl]benzotriazol,
2-(3-t-butyl-2-hydroxy-5-methylphenyl)-5-chlorobenzotriazol,
2-(3,5-di-t-butyl-2-hydroxyphenyl)-5-chlorobenzotriazol,
2-(3,5-di-t-butyl-2-hydroxyphenyl)benzotriazol,
2-(3,5-di-t-amyl-2-hydroxyphenyl)benzotriazol,
2-(2-hydroxyphenyl-5-t-octylphenyl)benzotriazol,
2-[2-hydroxy-3,5-bis($\alpha,\alpha$-dimethylbenzyl)phenyl]-2H-benzotriazol,
2,2'-methylenebis[6-(2H-benzotriazol-2-yl)-4-(1,1,3,3 -tetramethylbutyl)phenol], 2,2'-methylenebis[4-t-butyl-6-(2H-benzotriazol-2-yl)phenol], condensate of poly (ethylene glycol) and methyl 3-[3-(2H-benzotriazol-2-yl)-5-t-butyl-4-hydroxyphenyl]propionate, 2-ethylhexyl 3-[3-t-butyl-5-(5-chloro-2H-benzotriazol-2-yl)-4-hydroxyphenyl]propionate, octyl 3-[3-t-butyl-5-(5-chloro-2H-benzotriazol-2-yl)-4-hydroxyphenyl]propionate, methyl 3-[3-t-butyl-5-(5-chloro-2H-benzotriazol-2-yl)-4-hydroxyphenyl]propionate, 3-[3-t-butyl-5-(5-chloro-2H-benzotriazol-2-yl)-4-hydroxyphenyl]propionic acid, and the like.

Other types of ultraviolet absorbers are also usable in the present invention. Examples of the other types of ultraviolet absorbers include a benzoate-type ultraviolet absorber, such as 2,4-di-t-butylphenyl 3,5-di-t-butyl-4-hydroxybenzoate, cyanoacrylate-type ultraviolet absorber, such as ethyl 2-cyano-3,3-diphenylacrylate, oxamide-type ultraviolet absorber, such as N-(2-ethoxyphenyl)-N'-(2-ethylphenyl)oxamide, and the like.

Examples of the hindered amine type light stabilizer usable together with the piperidine compound in the present invention include:

bis(2,2,6,6-tetramethyl-4-piperidyl)sebacate,
bis(1,2,2,6,6-pentamethyl-piperidyl)sebacate,
N,N'-bis(2,2,6,6-tetramethyl-4-piperidyl)hexamethylenediamine,
tetrakis(2,2,6,6-tetramethyl-4-piperidyl) 1,2,3,4-butanetetracarboxylate,
poly[{6-(1,1,3,3-tetramethylbutyl)imino-1,3,5-triazine-2,4-diyl}{(2,2,6,6-tetramethyl-4-piperidyl)imino}hexamethylene{(2,2,6,6-tetramethyl-4-piperidyl)imino}],
poly[(6-morpholino-1,3,5-triazine-2,4-diyl){(2,2,6,6-tetramethyl-4-piperidyl)imino}hexamethylene{(2,2,6,6-tetramethyl-4-piperidyl)imino}],
polycondensate of dimethyl succinate and 1-(2-hydroxyethyl)-4-hydroxy-2,2,6,6-tetramethyl-piperidine,
N,N',4,7-tetrakis[4,6-bis{N-butyl-N-(1,1,2,6,6-pentamethyl-piperidyl)amino}-1,3,5-triazine-2-yl]-4,7-diazadecane-1,10-diamine,
and the like.

Known devices and known methods can be used for blending the piperidine compound and other additives, if desired, as stabilizers to the organic material in the present invention. For example, if the organic material is a solid polymer, the stabilizer may be dry-blended or may be blended in a form of a solution, a suspension or an emulsion. If the organic material is a synthetic polymer, it may be blended in the course of preparation of the polymer.

In this case, the stabilizer may be added either during the polymerization or immediately after the completion of polymerization, either directly or in a form of a solution, a suspension or an emulsion. If the organic material is liquid, such as oil, the stabilizer may be blended to the liquid either directly or in a form of concentrated solution prepared by dissolving the stabilizer into a liquid medium, such as oil.

The present invention will be described in more detail below with reference to Examples, but it is not limited thereto. In the following examples, "part" means "part by weight" unless otherwise mentioned.

EXAMPLE 1

Into a 3 liter flask, 1560 g of 4-amino-2,2,6,6-tetramethylpiperidine was placed. After the temperature was raised to 145° C., 430 g of methacrylic acid was added dropwise thereto. The inner temperature rose gradually and then the reaction mixture was kept at 170°±5° C., while collecting water distilled off, until the water collected had amounted to 90 g. Then the reaction mixture was cooled down to 50° C., and 500 g of acetone was added to the mixture to obtain a light yellowish slurry. The slurry thus obtained was cooled down to 20° C. and filtered. The filter cake was washed with acetone and dried to obtain 1053 g of pure white 2-methyl-3-(2,2,6,6-tetramethyl-4-piperidylamino)-N-(2,2,6,6-tetramethyl-4-piperidyl)propionamide (hereinafter referred to as Compound 1). M.p.: 115.5°–116.5° C. Mass spectrometry (FD-MS): m/z 380 (M$^+$).

Stabilizing tests were carried out by using Compound 1 and, for comparison, the following compounds:

HALS-1: bis(2,2,6,6-tetramethyl-4-piperidyl)sebacate,
HALS-2: polycondensate of dimethyl succinate and-1-(2-hydroxyethyl)-4-hydroxy-2,2,6,6-tetramethylpiperidine.

EXAMPLE 2

Using polypropylene as the organic material, compounding ingredients shown below were dry-blended.

| Compounding composition | |
| --- | --- |
| Polypropylene | 100 parts |
| Calcium stearate | 0.05 part |
| Phenolic-type antioxidants *1 | 0.05 part |
| Phosphorous containing antioxidants *2 | 0.05 part |
| Test compound | |
| Compound 1 | shown in Table 1 |
| HALS-1 | shown in Table 1 |

*1 pentaerythrityl tetrakis[3-(3,5-di-t-butyl-4-hydroxyphenyl) propionate]
*2 tris(2,4-di-t-butylphenyl) phosphite Each of the dry-blended mixture was melt-kneaded by using a monoaxial extruder, having the diameter of the cylinder being 30 mm, at 230° C. to form the pellets. The pellet thus formed was shaped into a plaque with 1 mm thickness by using an injection molding machine at 230° C. The plaque was put in Sunshine Weather-O-meter (produced by SUGA SHIKENKI Co. Ltd.), irradiated with light (light source: carbon arc, black panel temperature: 83°±3° C., water spray time of 18 minutes per 120 minutes cycle) and the period of time which had elapsed until cracks were generated on the irradiated surface was measured. The longer period of time indicates superior light stabililty.

The results are shown in Table 1.

TABLE 1

| | Example of the present invention | Comparative Example | |
| --- | --- | --- | --- |
| No. | 1-1 | 1-2 | 1-3 |
| Test compound | | | |
| Compound 1 | 0.2 part | — | — |
| HALS-1 | — | — | 0.2 part |
| Life time* (hours) | 780 | 180 | 720 |

*period of time which had elapsed until cracks were generated on the irradiated surface.

EXAMPLE 3

Using polyvinylchloride as the organic material, compounding ingredients shown below were dry-blended.

| Compounding composition | |
|---|---|
| Polyvinylchloride resin | 100 parts |
| Dioctylphthalate | 33 parts |
| Epoxide soybean oil | 2 parts |
| KV-403C *1 | 1.5 part |
| KP-902U *2 | 0.5 part |
| Test compound | |
| Compound 1 | shown in Table 2 |
| HALS-1 | shown in Table 2 |

*1 Barium-zinc containing liquid stabilizer; manufactured by Kyodo Chemical Co., Ltd.
*2 Barium-zinc containing powder stabilizer; manufactured by Kyodo Chemical Co., Ltd.

Each of the dry-blended mixture was heat-kneaded by using a 6 inch roll at 170° C. for 7 minutes to form a film with 0.2 mm thickness. The film thus formed was put in Geer oven at 190° C. and the period of time which had elapsed until the film blackened was measured. The longer period of time indicates superior heat resistance. (This test is referred to as Geer oven test.)

A film same to above-mentioned was cut into thin pieces and the thin pieces were placed in a test tube. Congo-Red test paper wetted with glycerin held by an absorbent cotton was placed into the test tube. Then a lid was put on the test tube and the test tube was dipped in an oil bath at 190° C. The period of time which had elapsed until the Congo-Red test paper started turning to blue due to the dehydrochlorination was measured. Polyvinylchloride generates hydrogenchloride gas on the deterioration and the hydrogenchloride gas makes the Congo-Red test paper turn into blue. Accordingly the longer period of time indicates superior thermal stability (This test is referred to as Congo Red test.)

Three of the films obtained above were pressed together by using a press machine at 165° C. to form a press sheet. The press sheet was placed into Eye super UV tester (manufactured by Iwasaki Electric Co. Ltd), test was conducted for 10 cycles at 63° C., one cycle being 4 hours of irradiation and keeping in wet state without irradiation for 4 hours, and then the hue of the sheet was observed. Less discoloration indicates superior light stability. (This test is referred to as UV test.)

The results are shown in Table 2.

TABLE 2

| | Example of the present invention | | Comparative Example | | |
|---|---|---|---|---|---|
| No. | 2-1 | 2-2 | 2-3 | 2-4 | 2-5 |
| Test compound (parts) | | | | | |
| Compound 1 | 0.03 | 0.05 | — | — | — |
| HALS-1 | — | — | — | 0.03 | 0.05 |
| Thermal stability | | | | | |
| Geer oven test (minutes) | 70 | 80 | 50 | 55 | 60 |
| Congo Red test (seconds) | 3498 | 3579 | 2741 | 3015 | 3110 |
| Light stability | | | | | |
| UV test | slight | slight | brown | yellow | slight |

TABLE 2-continued

| | Example of the present invention | | Comparative Example | | |
|---|---|---|---|---|---|
| No. | 2-1 | 2-2 | 2-3 | 2-4 | 2-5 |
| (hue after 10 cycles) | yellowish-brown | yellow | | -ish brown | yellowish brown |

EXAMPLE 4

Using polyvinylchloride as the organic material, compounding ingredients shown below were dry-blended.

| Compounding composition | |
|---|---|
| Polyvinylchloride resin | 100 parts |
| Dioctylphthalate | 80 parts |
| Epoxide soybean oil | 2 parts |
| Zinc stearate | 0.65 part |
| Barium stearate | 0.8 part |
| Dipentacrythritoladipate | 0.3 part |
| KV-67M-1 *1 | 1.0 part |
| ARUKAMIZER-5 *2 | 0.25 part |
| Test compound | |
| Compound 1 | shown in Table 3 |
| HALS-1 | shown in Table 3 |
| HALS-2 | shown in Table 3 |

*1 Barium-zinc containing liquid stabilizer; manufactured by Kyodo Chemical Co., Ltd.
*2 Hydrotalcite containing perchlorate; manufactured by Kyowa Chemical Co., Ltd.

By using each of the above dry-blended mixture and according to the same condition as in Example 3, a film with 0.2 mm thickness was formed. Using the film thus formed, Geer oven test and Congo Red test were conducted according to the same condition as in Example 3, except that Geer oven test was conducted at 195° C.

The results were shown in Table 3.

TABLE 3-1

| | Example of the present invention | | Comparative Example |
|---|---|---|---|
| No. | 3-1 | 3-2 | 3-3 |
| Test compound | | | |
| Compound 1 | 0.03 part | 0.05 part | — |
| HALS-1 | — | — | — |
| HALS-2 | — | — | — |
| Thermal stability | | | |
| Geer oven test (minutes) | 70 | 75 | 55 |
| Congo Red test (seconds) | 5073 | 5182 | 4447 |

TABLE 3-2

| | Comparative Example | | | |
|---|---|---|---|---|
| No. | 3-4 | 3-5 | 3-6 | 3-7 |
| Test compound | | | | |
| Compound 1 | — | — | — | — |

TABLE 3-2-continued

| | Comparative Example | | | |
|---|---|---|---|---|
| No. | 3-4 | 3-5 | 3-6 | 3-7 |
| HALS-1 | 0.03 part | 0.05 part | — | — |
| HALS-2 | — | — | 0.03 part | 0.05 part |
| Thermal stability | | | | |
| Geer oven test (minutes) | 60 | 65 | 60 | 65 |
| Congo Red test (seconds) | 4755 | 4775 | 4711 | 4759 |

2-Methyl-3-(2,2,6,6-tetramethyl-4-piperidylamino)-N-(2,2,6,6-tetramethyl-4-piperidyl)-propionamide of the present invention has excellent properties as a stabilizer for various types of organic materials, such as thermoplastic resins. Particularly, the compound imparts excellent light stability and thermal stability to the organic materials containing the compound. This compound also has an advantage that it is easily produced through common reactions, i.e. addition reaction and dehydrateamidation and from commonly-used starting materials, i.e. 4-amino-2,2,6,6-tetramethyl-4-piperidine and methacrylic acid.

What we claim is:

1. 2-Methyl-3-(2,2,6,6-tetramethyl-4-piperidylamino)-N-(2,2,6,6-tetramethyl-4-piperidyl)-propionamide.

* * * * *